United States Patent
Klok et al.

(10) Patent No.: US 11,279,619 B2
(45) Date of Patent: Mar. 22, 2022

(54) PROCESS TO CONVERT A SULPHUR COMPOUND

(71) Applicant: PAQELL B.V., Utrecht (NL)

(72) Inventors: Johannes Bernardus Maria Klok, Rhenen (NL); Margo Elzinga, Renkum (NL); Annemiek Ter Heijne, Rhenen (NL); Cees Jan Nico Buisman, Harich (NL); Johannes Wijnbelt, Amsterdam (NL)

(73) Assignee: PAQELL B.V., Utrecht (NL)

( * ) Notice: Subject to any disclaimer, the term of this patent is extended or adjusted under 35 U.S.C. 154(b) by 0 days.

(21) Appl. No.: 17/058,180

(22) PCT Filed: May 29, 2019

(86) PCT No.: PCT/EP2019/064053
§ 371 (c)(1),
(2) Date: Nov. 24, 2020

(87) PCT Pub. No.: WO2019/229167
PCT Pub. Date: Dec. 5, 2019

(65) Prior Publication Data
US 2021/0139327 A1    May 13, 2021

(30) Foreign Application Priority Data
Jun. 1, 2018 (EP) .................................. 18175559

(51) Int. Cl.
*B01D 53/73* (2006.01)
*B01D 53/84* (2006.01)
(Continued)

(52) U.S. Cl.
CPC .............. *C01B 17/18* (2013.01); *B01D 53/73* (2013.01); *B01D 53/84* (2013.01); *C12P 3/00* (2013.01);
(Continued)

(58) Field of Classification Search
CPC ........ B01D 53/1487; B01D 2257/7027; B01D 53/1468; B01D 2257/304; B01D 53/84;
(Continued)

(56) References Cited

U.S. PATENT DOCUMENTS

| | | | |
|---|---|---|---|
| 8,900,840 B2 * | 12/2014 | Hafez | .................... C12M 33/22 435/167 |
| 2009/0317882 A1 | 12/2009 | Cheng et al. | |
| 2010/0252443 A1 | 10/2010 | Borole | |

FOREIGN PATENT DOCUMENTS

| | | | |
|---|---|---|---|
| KR | 2019 123 513 A * | 11/2019 | ............. B01D 53/84 |
| WO | 1992010270 A1 | 6/1992 | |

OTHER PUBLICATIONS

Enzmann et al. "Methanogens: biochemical background and biotechnological applications." AMB Express 8(1): 1-22 (2018).
(Continued)

*Primary Examiner* — Timothy C Vanoy
(74) *Attorney, Agent, or Firm* — Nixon Peabody LLP; Ronald I. Eisenstein; Nicole D. Kling

(57) ABSTRACT

The invention is directed to a process to convert a sulphur compound to bisulphide by direct or indirect transfer of electrons from a cathode of a bio-electrochemical cell to the sulphur compound under anaerobic conditions and in the presence of mixed culture comprising methanogens and suitably also a anaerobic or facultative anaerobic bacteria. The sulphur compound may be a thiol like methanethiol or ethanethiol or a polysulphide, like dimethyl disulphide.

32 Claims, 1 Drawing Sheet

(51) Int. Cl.
   *C01B 17/18* (2006.01)
   *C12P 3/00* (2006.01)
   *C25B 1/01* (2021.01)

(52) U.S. Cl.
   CPC .......... *C25B 1/01* (2021.01); *B01D 2256/24* (2013.01); *B01D 2257/304* (2013.01); *B01D 2257/306* (2013.01); *B01D 2257/7027* (2013.01)

(58) Field of Classification Search
   CPC .......... B01D 2257/306; B01D 2256/24; B01D 53/73; B01D 2258/05; B01D 53/326; B01D 53/72; B01D 2256/245; C12P 3/00; C25B 3/25; C25B 11/04; C25B 1/01; C25B 9/17; Y02A 50/20; C01B 17/18; C01B 17/20; C07C 1/322; C07C 9/04
   See application file for complete search history.

(56) References Cited

OTHER PUBLICATIONS

Ellis et al. "Characterization of a methanogenic community within an algal fed anaerobic digester." ISRN microbiology 2012: 1-12 (2012).

Siegert et al. "Comparison of nonprecious metal cathode materials for methane production by electromethanogenesis." ACS Sustainable Chemistry & Engineering 2(4): 910-917 (2014).

* cited by examiner

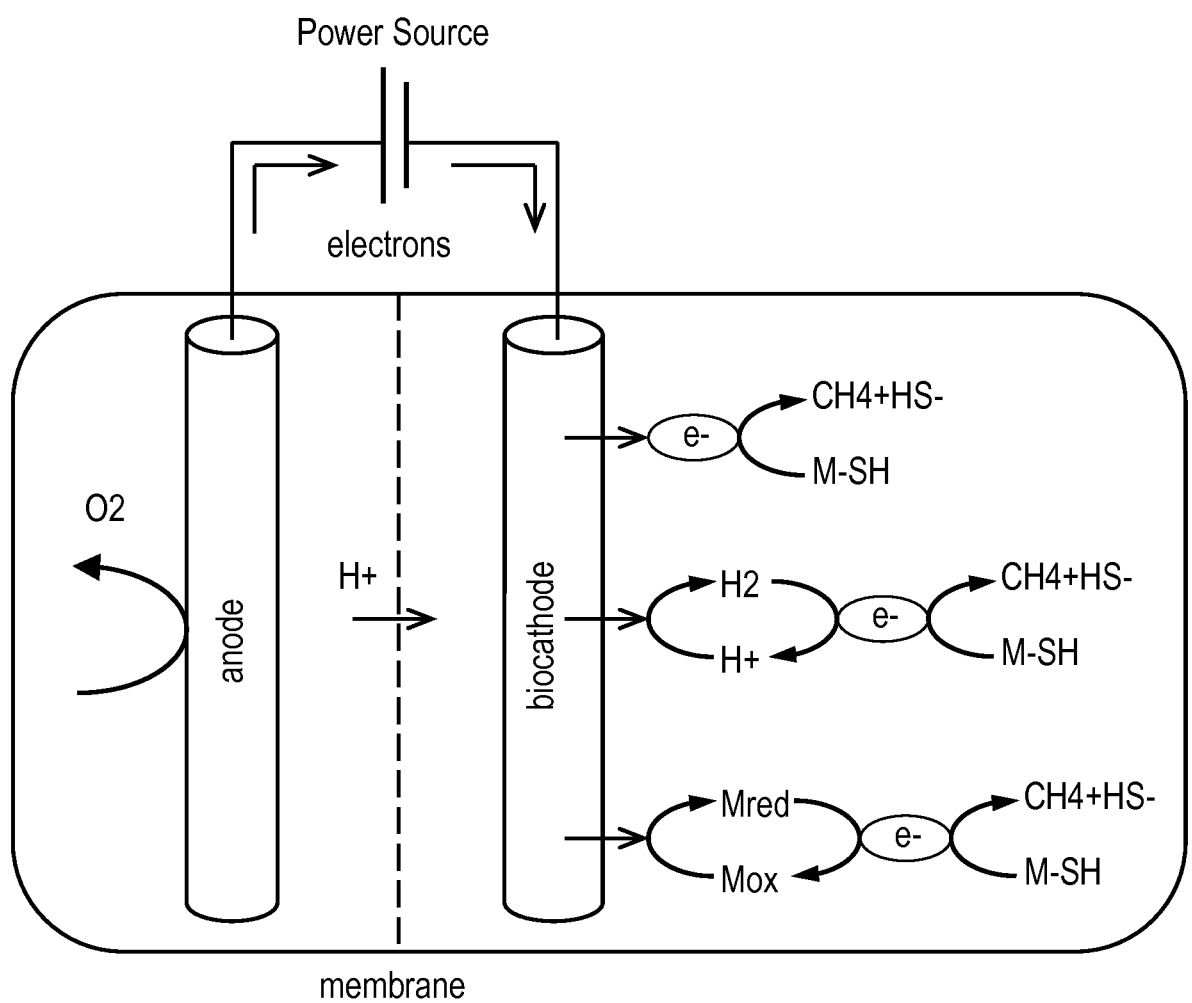

PROCESS TO CONVERT A SULPHUR COMPOUND

CROSS-REFERENCE TO RELATED APPLICATIONS

This application is a 35 U.S.C. § 371 National Phase Entry Application of International Application No. PCT/EP2019/064053 filed May 29, 2019, which designates the U.S. and claims benefit under 35 U.S.C. § 119(a) of EP Provisional Application No. 18175559.6 filed Jun. 1, 2018, the contents of which are incorporated herein by reference in their entireties.

FIELD OF THE INVENTION

The invention is directed to a process to convert a sulphur compound and especially mercaptans and disulphides.

BACKGROUND OF THE INVENTION

Mercaptans and disulphides are compounds which may be present in for example natural gas, refinery gaseous streams, like fuel gas, and liquid streams like for example LPG. The removal of such organosulphur compounds and especially mercaptans (thiols) is desired because of corrosion risks, smell and/or toxicological reasons.

The removal of especially mercaptans from hydrocarbon streams is a major challenge as reported in Bloemendaal G., Kobussen S., Scheel F., Capture and Convert, Hydrocarbon Engineering, December 2008. In this overview article various processes are described to isolate and convert mercaptans from refinery streams and natural gas. In one of the processes described in this article mercaptans are absorbed from a gas using a caustic solution and subsequently oxidised to a disulphide oil using a Merox catalyst in a so-called Merox process developed by UOP. A disadvantage of such a process is that it not only involves numerous steps and chemical consumption but also forms a disulphide oil which has to be further processed. Such further processing is typically a hydrotreater where the disulphide oil is converted to $H_2S$. This is one illustration of the complex processing required to convert mercaptans to $H_2S$.

Ellis, Joshua & Tramp, Cody & Sims, Ronald & Miller, Charles. (2012). Characterization of a Methanogenic Community within an Algal Fed Anaerobic Digester. ISRN microbiology. 2012. 753892 described a process to reduce methyl mercaptan towards bisulfide and methane in an anaerobic digestion process. A problem with this process is that only methyl mercaptan was successfully reduced and that the degradation rates were limited which would result in long hydraulic retention times in practical applications.

There is thus a desire for a process which can convert a variety of sulphur compounds and especially a variety of mercaptans in a more simpler manner.

BRIEF DESCRIPTION OF THE FIGURE

FIG. 1: a schematic diagram of the conversion of methanethiol (M-SH) to sulphide and methane by indirect and direct transfer of electrons from a cathode of a bio-electrochemical cell to the sulphur compound under anaerobic conditions. e-denotes microorganisms; $M_{red/ox}$ is a redox mediator which can transfer charge from an electrode to a reactant.

DETAILED DESCRIPTION

The present invention relates to a process to convert a sulphur compound to bisulphide by direct or indirect transfer of electrons from a cathode of a bio-electrochemical cell to the sulphur compound under anaerobic conditions and in the presence of methanogens. In addition, anaerobic or facultative anaerobic bacteria may be present. This process is much simpler than existing processes for converting sulphur compounds.

In one embodiment the process comprises: a) inoculating a bio-electrochemical cell with a mixed culture of microorganisms obtained from an anaerobically grown culture, the mixed culture comprising methanogens; b) contacting the mixed culture of microorganisms with an organic sulphur compound; c) allowing the mixed culture of microorganisms to convert the organic sulphur compound to bisulphide.

Applicants found that such a process can effectively convert sulphur compounds to bisulphide, and thus convert toxic compounds to less toxic compounds. Using the process according to the invention, the levels of organic sulphur compound may be reduced to below 100 ppm, preferably below 50 ppm, more preferably below 20 ppm or below 10 ppm.

The skilled person will understand that bisulphide ($HS^-$) will be in chemical equilibrium with sulfide ($S^{2-}$) and hydrogen sulphide ($H_2S$). At the prevailing pH, which is between about pH 8.5 and about pH 10, more than 80% of the sulphide will be in the form of bisulphide ($HS^-$).

Bisulphide itself can be easily converted to elemental sulphur by known processes or discharged as a $H_2S$ rich gas.

The sulphur compound is suitably a mercaptan compound, further referred to as thiol. The thiol compound may have the general formula R—SH, wherein R may be an alkyl, aryl, arylalkyl or alkylaryl group. The alkyl group may be a C1 to C4 alkyl group. In a typical natural gas or crude oil derived gaseous stream the major thiols are methanethiol, ethanethiol and propanethiol. Applicants found that the process is suited to convert ethanethiol and propanethiol, which compound has been found to be difficult to convert using prior art processes. Thus the thiol compound converted by the process is suitably ethanethiol, alone or in a mixture comprising other sulphur compounds.

The sulphur compound may also be a polyorgano polysulphide (POPS). The polyorgano polysulphide may be the disulphide oil as obtained in the earlier referred to Merox process. The process provides a simpler alternative for the usual hydrotreating step. The polyorgano polysulphide compound may also be formed as an intermediate compound when thiols are converted by the process according to the invention. Such polyorgano polysulphide compounds will then also be converted to bisulphide in the bio-electrochemical cell. Examples of possible polyorgano polysulphides are dimethyl disulphide, diethyl disulphide, dimethyl trisulphide and ethyl methyl disulphide.

The process is performed in a bio-electrochemical cell, also referred to as BES, comprising an anode as present in an anode compartment and a cathode as present in a cathode compartment. The anode and cathode will be submerged in an aqueous solution in the respective compartments. Depending on the bio-electrochemical cell design of the anode and the composition of the aqueous solution into which the anode is submerged the electrochemical cell may produce an electrical current running from cathode to anode. Such a current may also be generated by applying an electric potential difference between the anode and cathode.

The anode and cathode may be present in the same space, more specifically in the same vessel. Preferably the anode compartment is separated from the cathode compartment by a semi-permeable membrane. Such a membrane may be an ion-selective membrane for transport of cations from anode to cathode. Such cations may be any cation which is present in higher concentrations. Examples of cations are H⁺ and Na⁺. The membrane may also be an ion-selective membrane for transport of anions from cathode to anode. Examples of anions are OH⁻ or HCO₃⁻. The membrane may also be a bipolar membrane.

The bio-electrochemical cell may be a single cell or a multitude of cells which may be arranged in parallel and/or in series with respect to each other.

The material of the anode may be any conductive material. Preferably the anode is provided with a so-called mixed metal coating to avoid dissolution of the anode material. Such anodes are referred to as dimensionally stable anodes (DSA). Examples of suitably conductive materials for the anode are stainless steel, titanium and carbon based materials or preferably graphite. At the anode electrons may be transferred to the anode by the following reaction:

$$2H_2O \rightarrow O_2 + 4H^+ + 4e^-$$

The material of the cathode may be graphite-based or carbon-based (uncatalyzed) or metal-based, like for example stainless steel. Examples of catalyzed cathodes are mixed metal oxide coatings containing Pt, Ir, or other noble metals, on a conductive support like titanium. Possible catalysts are Pt, Ir and Cu.

Without wishing to be bound by theory, it is believed that at the cathode electrons may be transferred from the cathode to methanogens, which reduce the sulphur compound according to the following illustrative reactions 1-4, either taking up electrons directly or via hydrogen or another redox mediator:

$$CH_3SH + 2e^- \rightarrow CH_4 + S^{2-} \qquad (1)$$

$$C_2H_5SH + 2H^+ + 4e^- \rightarrow 2CH_4 + S^{2-} \qquad (2)$$

$$C_3H_7SH + 4H^+ + 6e^- \rightarrow 3CH_4 + S^{2-} \qquad (3)$$

$$C_2H_6S_2 + 2H^+ + 4e^- \rightarrow 2CH_4 + 2S^{2-} \qquad (4)$$

for methanethiol (1), ethanethiol (2), propanethiol (3) and dimethyl disulphide (DMDS)(4). The sulfide (S²⁻) is in chemical equilibrium with bisulphide (HS—).

The reaction at the cathode takes place in the presence of a mixed culture of microorganisms obtained from an anaerobically grown culture, the mixed culture comprising methanogens. Therefore, in one embodiment, the process comprises converting a sulphur compound to bisulphide by direct or indirect transfer of electrons from a cathode of a bio-electrochemical cell to the sulphur compound under anaerobic conditions and in the presence of methanogens.

Examples of suitable methanogens are *Methanobacterium bryantii*; *Methanobacterium formicum*; *Methanobrevibacter arboriphilicus*; *Methanobrevibactergottschalkii*; *Methanobrevibacter ruminantium*; *Methanobrevibacter smithii*; *Methanocalculus chunghsingensis*; *Methanococcoides burtonii*; *Methanococcus aeolicus*; *Methanococcus deltae*; *Methanococcus jannaschii*; *Methanococcus maripaludis*; *Methanococcus vannielii*; *Met hanocorpusculum labreanum*; *Methanoculleus bourgensis*; *Methanogenium olentangyi*; *Methanogenium bourgense*; *Methanoculleus marisnigri*; *Methanofollis liminatans*; *Methanogenium cariaci*; *Methanogenium frigidum*; *Methanogenium organophilum*; *Methanogenium wolfei*; *Methanomicrobium mobile*; *Methanopyrus kandleri*; *Methanoregula boonei*; *Methanosaeta concilii*; *Methanosaeta thermophila*; *Methanosarcinaacetivorans*; *Methanosarcina barkeri*; *Methanosarcina mazei*; *Methanosphaera stadtmanae*; *Methanospirillum hungatei*; *Methanothermobacterdefluvii*; *Methanothermobacter thermautotrophicus*; *Methanothermobacter thermoflexus*; *Methanothermobacter wolfei*; *Methanothrix soehngenii*; *Methanobacterium palustre*; and combinations of any of these and/or other methanogens. Methanogens may be provided as a purified culture, enriched in methanogens, or even enriched in a specified species of methanogen, if desired.

In one embodiment, in addition to methanogens, further microorganisms are present, including anaerobic or facultative anaerobic bacteria. Therefore, in one embodiment, the process comprises converting a sulphur compound to bisulphide by direct or indirect transfer of electrons from a cathode of a bio-electrochemical cell to the sulphur compound under anaerobic conditions and in the presence of 50-90% (based on total 16S rRNA analysis) methanogens and suitably also anaerobic or facultative anaerobic bacteria. Anaerobic microorganisms do not require of oxygen for growth. Facultative anaerobic microorganisms are able to grow under both aerobic and anaerobic conditions. Suitable anaerobic or facultative anaerobic bacteria may be selected from one or more families of the group of Halomonadaceae, Clostridiaceae 2, ldiomarinaceae, Peptostreptococcaceae, Eubacteriaceae, Rhodobacteraceae, Synergistaceae, ML635J-40 aquatic group, Spirochaetaceae, Erysipelotrichaceae, Ectothiorhodospiraceae and Thermoanaerobacterales Family XIV.

The mixed cultures is preferably obtained from an anaerobic system, such as an anaerobically grown culture. The mixed culture may therefore be obtained from the sludge of an anaerobic bioreactor, such as an anaerobic fermenter, for example one used for anaerobic chain elongation; an anaerobic digestion reactor, for example an upflow anaerobic sludge blanket reactor (UASB); an anaerobic reduction reactor, for example for (thio)sulphate reduction; or an anaerobic resource recovery reactor, for example as used for selenite reduction. Other suitable bioreactors for providing the sludge are expended granular sludge bed (EGSB), a sequential batch reactor (SBR), a continuously stirred tank reactor (CSTR) or an anaerobic membrane bioreactor (AnMBR). In one embodiment, the mixed cultures are taken from a bioreactor fed with influent high in methanol (~200 mM) or from anaerobic sludge obtained from a municipal wastewater treatment plant. In the present context, the term sludge refers to the semi-solid flocs or granules containing a mixed culture of microorganisms.

The cathode of the bio-electrochemical cell will suitably be in contact with an aqueous solution, the catholyte, which solution will comprise the sulphur compound which is converted. Methanogens and suitably also bacteria may be present in the catholyte as planktonic cells and/or as a biofilm on the surface of the cathode. Alkanols, like methanol, may be added to the catholyte as an activator for the methanogens. The temperature may range from lower temperatures just above the solidification point of the catholyte to high temperatures. Good results have been achieved at ambient temperatures, which is one of the advantages of the current invention. The pressure may range from sub-atmospheric pressure to higher pressures. If not required by upstream or downstream processes the pressure is preferably around ambient pressure which is one of the advantages of the current invention. The current density in the bio-electrochemical cell may range from 0.1 to 500 A/m² projected electrode surface area at a cathode potential versus an Ag/AgCl electrode of between 0 and −2 V.

Anaerobic conditions are suitably achieved by performing the process in the absence of molecular oxygen, preferably also in the absence of other oxidants such as for example nitrate. By 'in the absence of molecular oxygen' is meant that the concentration of molecular oxygen in the aqueous reaction medium is at most 10 µM molecular oxygen, preferably at most 1 µM, more preferably at most 0.1 µM molecular oxygen.

Suitably the sulphur compound is present in an aqueous mixture as obtained by absorption between an aqueous solution poor in sulphur compounds and a starting gaseous mixture comprising sulphur compounds thereby obtaining a gas poor in sulphur compounds. Such an absorption may be performed in a separate absorption step. This is especially preferred when the pressure of the starting gas is substantially higher than the pressure in the bio-electrochemical cell. Alternatively the absorption may take place in the bio-electrochemical cell itself. In the latter case a starting gaseous mixture comprising sulphur compounds may be passed as a disperse phase through the aqueous mixture contacting the cathode of the bio-electrochemical cell. Such a gaseous mixture comprising sulphur compounds may be a hydrocarbon rich gas like natural gas or a refinery gas, like for example fuel gas or a biogas, for example obtained in a fermentation process of manure. Such a gas may further comprise hydrogen sulphide and/or carbon dioxide. The gas may be obtained in a selective hydrogen sulphide absorption step wherein the obtained gas poor in hydrogen sulphide may still contain sulphur compounds like thiols and/or bisulphide compounds. The gas may also be an acid gas comprising high contents of hydrogen sulphide and optionally carbon dioxide.

The bisulphide as formed is suitably removed from the aqueous solution by desorption between the aqueous solution and the earlier referred to gas poor in sulphur compounds thereby obtaining a lean aqueous solution. Alternatively, the bisulphide is removed from the aqueous solution by desorption between the aqueous solution and a different gas stream. In this manner a more hydrogen sulphide rich stream may be obtained which can be easier used as a feed to a further bisulphide conversion process.

The lean aqueous solution may be subsequently used in the absorption step as the aqueous solution poor in sulphur compounds The gaseous stream used in the desorption step may be the gaseous stream or part of the gas stream poor in sulphur compounds obtained in the above referred to absorption step.

The gaseous mixture comprising sulphur compounds may also be directly fed to the cathode. Preferably the cathode is a gas diffusion electrode (GDE) in such an embodiment. Gas diffusion electrodes are known and for example described in US2016164120. In such a gas diffusion electrode the sulphur compounds in the gas may be converted to bisulphide compounds and hydrogen sulphide. The hydrogen sulphide may be discharged with the exit gas leaving the gas diffusion electrode. The application of such a gas diffusion electrode is advantageous because this would result in that the earlier referred to absorption may be performed at a smaller scale or even may not be required at all.

Preferably the above processes are performed as a continuous process. The conversion of the thiol into bisulphide, or into one of its equilibrium sulphide forms, may be confirmed by lead acetate, for example by lead acetate paper. Lead acetate paper does not react with thiol, but will react with free sulphide, in any of it forms, viz. sulphide, bisulphide or hydrogen sulphide.

The formed bisulphide compound is preferably converted to elemental sulphur in a further process. Examples of bisulphide conversion processes yielding elemental sulphur are the liquid redox process as offered by Merichem and the biological oxidation of bisulphide as for example the Thiopaq O&G offered by Pagell. Examples of suitable biological oxidation processes are described in WO92/10270, WO94/29227, WO2005/092788 and WO2015114069.

Applicants found that benzene, toluene, ethylbenzene and/or xylene may also be converted by direct or indirect transfer of electrons from the cathode of the bio-electrochemical cell to benzene, toluene, ethylbenzene and/or xylene in the above described process. These compounds may be converted to methane. Thus any of such compounds may be converted when the sulphur compound is converted to bisulphide. It is found that such a conversion can also take place in the absence of a sulphur compound. The invention is therefore also directed to a process to convert benzene, toluene, ethylbenzene and/or xylene to methane by direct or indirect transfer of electrons from the cathode of the bio-electrochemical cell to benzene, toluene, ethylbenzene and/or xylene under anaerobic conditions and in the presence of methanogens as described above for the sulphur compounds.

The invention shall be illustrated using the following FIG. 1. FIG. 1 is a schematic diagram of the conversion of methanethiol (M-SH) to sulphide and methane by transfer of electrons from a cathode of a bio-electrochemical cell to the sulphur compound under anaerobic conditions and in the presence of methanogens, and suitably also anaerobic or facultative anaerobic bacteria, represented as the circles with the e−. At the biocathode three possible pathways are shown for this conversion in which $M_{red/ox}$ is a redox mediator which can transfer charge from an electrode to a reactant. Examples of possible redox mediators are H2, Methyl Viologen and Methylene Blue. In this Figure it is shown that electrons flow from the cathode via the microorganisms to methanethiol. At the anode water is oxidized into $O_2$ and electrons flow from the anode to the biocathode via an external electric circuit. The reaction taking place at the anode may also be electrochemical reactions or reactions catalyzed by microorganisms, such as for example oxidation of acetate to CO2 and oxidation of inorganic components like sulphide, iron, or other metals.

The invention shall be illustrated making use of the following non-limiting examples.

EXAMPLE 1

A bio electrochemical reactor was used to study ethanethiol degradation. The bio electrochemical reactor had two chambers separated by a cation exchange membrane. Graphite felt were used as both anode (1 cm×2 cm×5 cm) and cathode (1 cm×2 cm×15 cm) electrodes. Platinum clamps were used as a current collector for both the anode and cathode. The reference electrode was a 3M KCl saturated Ag/AgCl electrode (+210 mV versus SHE). Each bio electrochemical reactor was galvanostatically controlled by a potentiostat (Ivium, the Netherlands) at a current of 2 mA. Gas production was collected in the gas bag (500 mL) for all reactors. All the reactors were operated inside a temperature controlled cabinet at 30° C.

The medium for biodegradation of organosulfur compounds consisted of (per liter): bicarbonate buffer with 49 g of $NaHCO_3$ and 4.42 g of $Na_2CO_3$, 0.1 mL of trace element solution. Final pH of the medium was around 8.5. All the reactors were filled with 120 mL of the medium, except the anode chamber of the bio electrochemical reactors. The anolyte contained only the same bicarbonate buffer and 100 mM of potassium hexacyanoferrate(II) trihydrate. Herein, the potassium hexacyanoferrate(II) trihydrate served as an electron donor.

Mixed cultures of microbiomes were taken from bioreactors fed with influent high in methanol (~200 mM) and anaerobic sludge obtained from a municipal wastewater treatment plant. 500 mL of the effluent of these bioreactors was concentrated by centrifugation with 5000 RPM for 10 min. It was washed with fresh medium for three times. Finally, 5 mL of the concentrated inoculum (in total 20 mL) was added into each reactor except for one, which served as a control without microorganisms. For anaerobic sludge, 7 mL was added to each reactor except for the abiotic control. The mixed cultures were analyzed using 16S rRNA analysis and comprised of methanogens. In addition to methanogens (based on total 16S rRNA analysis), further microorganisms were present, including Halomonadaceae, Clostridiaceae 2, ldiomarinaceae, Peptostreptococcaceae, Eubacteriaceae, Rhodobacteraceae, Synergistaceae, ML635J-40 aquatic group, Spirochaetaceae, Erysipelotrichaceae, Ectothiorhodospiraceae and Thermoanaerobacterales Family XIV.

One week after inoculation, the catholyte was spiked with 0.05 mmol of ethanethiol (ethanethiol) on Day 7 and Day 13. During the experiment, headspace composition was analyzed for $CO_2$, $H_2$, $O_2$, $CH_4$ by gas chromatography. pH of each reactor was regularly checked. Lead acetate paper was used as indicator for the presence of free sulphide, in any of its forms, as the final reduction product.

Sulphide production was found 7 hours after the first addition of ethanethiol, and 18 hours after the second addition of ethanethiol, indicating reduction of ethanethiol to sulphide.

Comparative Experiment A

Example 1 was repeated except that no methanogens were added. No conversion of ethanethiol was observed.

Comparative Experiment B

Example 1 was repeated in a bottle without electrodes. Microorganisms were present. No conversion of ethanethiol was observed.

Comparative Experiment C

Example 1 was repeated with microorganisms in the presence of a hydrogen and carbon dioxide gas mixture. No conversion of ethanethiol was observed.

EXAMPLE 2

Example 1 was repeated for 30 days and spiking was performed with 0.1 mM ethanethiol from day 7 to day 20 and increased from day 20 to day 30 to 0.2 mM. At day 33 the medium was partly replaced resulting in a lower thiol loading. Sulphide production was found after every addition of ethanethiol indicating reduction of ethanethiol to sulphide over a prolonged period of time.

EXAMPLE 3

Example 2 was repeated except that the catholyte was spiked with methane thiol instead of ethanethiol. Sulphide production was found after every addition of methanethiol indicating reduction of methanethiol to sulphide over a prolonged period of time.

EXAMPLE 4

Example 2 was repeated except that the catholyte was spiked with propanethiol instead of ethane thiol. Sulphide production was found after every addition of propane thiol indicating reduction of propyl thiol to sulphide over a prolonged period of time.

EXAMPLE 5

Example 1 was repeated except that the catholyte was spiked with dimethyl disulphide (DMDS) instead of ethanethiol. Sulphide production was found after every addition of DMDS indicating reduction of DMDS to sulphide over a prolonged period of time.

The invention claimed is:

1. A process for anaerobic bio-electrochemical degradation of an organic sulphur compound to bisulphide, comprising
   a) inoculating a bio-electrochemical cell with a mixed culture of microorganisms obtained from an anaerobically grown culture, the mixed culture comprising methanogens;
   b) contacting the microorganisms with an organic sulphur compound;
   c) allowing the microorganisms in the mixed culture to convert the organic sulphur compound to bisulphide by direct or indirect transfer of electrons from a cathode of the bio-electrochemical cell to the sulphur compound under anaerobic conditions.

2. The process according to claim 1, wherein the anaerobically grown culture is obtained from sludge of an anaerobic bioreactor.

3. The process of claim 2, wherein the anaerobic bioreactor is an upflow anaerobic sludge blanket reactor (UASB).

4. The process according to claim 2, wherein the anaerobic bioreactor was fed with an influent comprising 200 mM or more methanol.

5. The process according to claim 2, wherein the anaerobic bioreactor is an anaerobic fermenter, anaerobic digestion reactor, an anaerobic reduction reactor, or an anaerobic resource recovery reactor.

6. The process according to claim 1, wherein the anaerobically grown culture is obtained from a municipal waste water treatment plant.

7. The process according to claim 1, wherein the organic sulphur compound is a thiol or a polyorganic polysulphide compound.

8. The process according to claim 7, wherein the thiol compound is ethanethiol or propanethiol.

9. The process according to claim 8, wherein the thiol compound is ethanethiol, alone or in an admixture comprising other sulphur compounds.

10. The process according to claim 9, wherein the other sulphur compounds comprise propanethiol.

11. The process according to claim 7, wherein the polyorganic polysulphide compound is dimethyl disulphide (DMDS).

12. The process according to claim 1, wherein a toxic compound is converted into a less toxic compound.

13. The process according to claim 1, wherein the levels of the organic sulphur compound are reduced to below 100 ppm by conversion in the bio-electrical cell.

14. The process according to claim 1, wherein the conversion to disulphide is by indirect transfer of electrons from a cathode of the bio-electrochemical cell to the sulphur compound.

15. The process according to claim 1, wherein the process conditions are 30 deg C., 0.8 M Na+, and pH in the range of 8.5 and 10.

16. The process according to claim 1, which is conducted at a redox potential in the range of 0 and −2000 mV with respect to a standard Ag/AgCl electrode.

17. The process according to claim 1, wherein in addition to methanogens the mixed culture further comprises one or more microorganisms selected from the group consisting of: Halomonadaceae, Clostridiaceae 2, Idiomarinaceae, Peptostreptococcaceae, Eubacteriaceae, Rhodobacteraceae, Synergistaceae, ML635J-40 aquatic group, Spirochaetaceae, Erysipelotrichaceae, Ectothiorhodospiraceae, and Thermoanaerobacterales Family XIV.

18. The process according to claim 1, wherein the microorganisms in the mixed culture are cathodophilic.

19. The process according to claim 1, wherein the microorganisms are present in an aqueous solution in planktonic form in (c).

20. The process according to claim 1, wherein the microorganisms are present in a biofilm on the surface of the cathode.

21. The process according to claim 1, wherein the material of the surface of the cathode comprises carbon or a metal.

22. The process according to claim 1, further comprising an absorption step wherein organic sulphur compounds are absorbed from a starting gaseous mixture comprising sulphur compounds into an aqueous solution poor in sulphur compounds, thereby obtaining a gas poor in sulphur compounds and an aqueous mixture comprising the organic sulphur compound.

23. The process according to claim 22, wherein the bisulphide as formed is removed from the aqueous mixture by desorption between the aqueous solution and the gas poor in sulphur compounds, thereby obtaining a lean aqueous solution.

24. The process according to claim 23, wherein the lean aqueous solution is used in the absorption step as the aqueous solution poor in sulphur compounds.

25. The process according to claim 1, wherein the cathode is a gas diffusion electrode to which a gas comprising sulphur compounds is fed.

26. The process according to claim 1, wherein also benzene, toluene, ethylbenzene, or xylene are converted to methane by direct or indirect transfer of electrons from the cathode of the bio-electrochemical cell to benzene, toluene, ethylbenzene, or xylene.

27. The process according to claim 1, wherein the formed bisulphide is converted to elemental sulphur by biological oxidation of the bisulphide.

28. A process to convert a sulphur compound to bisulphide by direct or indirect transfer of electrons from a cathode of a bio-electrochemical cell to the sulphur compound under anaerobic conditions and in the presence of methanogens.

29. The process according to claim 28, further wherein anaerobic or facultative anaerobic bacteria are present.

30. The process according to claim 28, wherein the sulphur compound is ethanethiol, alone or in an admixture comprising other sulphur compounds.

31. The process according to claim 30, wherein the other sulphur compounds comprise propanethiol.

32. A method of anaerobic bio-electrochemical degradation of an organic sulphur compound to bisulphide, the method comprising contacting a mixed culture of microorganism from the sludge of an anaerobic bioreactor with an organic sulphur compound.

* * * * *